(12) United States Patent
Ekin

(10) Patent No.: US 10,786,309 B2
(45) Date of Patent: Sep. 29, 2020

(54) RADIATION-FREE REGISTRATION OF AN OPTICAL SHAPE SENSING SYSTEM TO AN IMAGING SYSTEM

(71) Applicant: KONINKLIJKE PHILIPS N.V., Eindhoven (NL)

(72) Inventor: Ahmet Ekin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 226 days.

(21) Appl. No.: 15/100,752

(22) PCT Filed: Dec. 2, 2014

(86) PCT No.: PCT/EP2014/076156
§ 371 (c)(1),
(2) Date: Jun. 1, 2016

(87) PCT Pub. No.: WO2015/086364
PCT Pub. Date: Jun. 18, 2015

(65) Prior Publication Data
US 2016/0296292 A1 Oct. 13, 2016

(30) Foreign Application Priority Data

Dec. 10, 2013 (EP) ..................... 13196480

(51) Int. Cl.
*A61B 34/20* (2016.01)
*A61B 6/12* (2006.01)
*A61B 90/00* (2016.01)
*A61B 18/14* (2006.01)
*A61B 17/00* (2006.01)
*A61B 18/00* (2006.01)

(52) U.S. Cl.
CPC ................ *A61B 34/20* (2016.02); *A61B 6/12* (2013.01); *A61B 18/1492* (2013.01);
(Continued)

(58) Field of Classification Search
CPC ... A61B 34/20; A61B 18/1492; A61B 90/361; A61B 6/12; A61B 2090/3937;
(Continued)

(56) References Cited

U.S. PATENT DOCUMENTS 6,006,126 A * 12/1999 Cosman ................. A61B 34/20
600/414
6,473,489 B2 1/2002 Bani-Hashemi et al.
(Continued)

FOREIGN PATENT DOCUMENTS

EP 2072012 A1 6/2009
WO 2007115825 A1 10/2007

OTHER PUBLICATIONS

Krissian, K., et al. "Model-Based Detection of Tubular Structures in 3D Images", Computer Vision and Image Understanding, vol. 80, No. 2, pp. 130-171 (2000).
(Continued)

*Primary Examiner* — Sanjay Cattungal

(57) ABSTRACT

The invention relates to a registration system (13) for registering an optical shape system to an imaging system with an imaging device (2) like a radiation C-arm device with a tracking device (4) like an optical shape sensing tracking device. One or more optical cameras (27) are used to detect position information of a tracked object to register the shape coordinate system with that of the imaging system. The optical cameras are pre-calibrated with the imaging system, so that the detected position information in the camera system can directly be translated to the imaging system.

18 Claims, 2 Drawing Sheets

(52) U.S. Cl.
CPC ............ *A61B 90/361* (2016.02); *A61B 90/39* (2016.02); *A61B 2017/00243* (2013.01); *A61B 2018/00351* (2013.01); *A61B 2034/207* (2016.02); *A61B 2034/2061* (2016.02); *A61B 2034/2065* (2016.02); *A61B 2090/367* (2016.02); *A61B 2090/3937* (2016.02); *A61B 2090/3954* (2016.02)

(58) Field of Classification Search
CPC ........... A61B 2017/00243; A61B 2018/00351; A61B 2090/3954; A61B 90/39; A61B 2034/2065; A61B 2034/2061; A61B 2090/367; A61B 2034/207
USPC ................................................. 600/407–480
See application file for complete search history.

(56) References Cited

U.S. PATENT DOCUMENTS

| | | | |
|---|---|---|---|
| 7,772,541 B2 | 8/2010 | Froggatt et al. | |
| 8,350,914 B2 | 1/2013 | Li et al. | |
| 2010/0056904 A1 | 3/2010 | Saunders et al. | |
| 2011/0098553 A1 | 4/2011 | Robbins et al. | |
| 2011/0255661 A1 | 10/2011 | Schweizer | |
| 2013/0033700 A1* | 2/2013 | Hallil | G01B 11/00 356/72 |
| 2013/0060146 A1* | 3/2013 | Yang | A61B 5/055 600/476 |
| 2014/0049629 A1 | 2/2014 | Siewerdsen et al. | |
| 2014/0357989 A1 | 12/2014 | Hendriks et al. | |
| 2018/0008351 A1* | 1/2018 | Schoenefeld | A61B 17/15 |
| 2018/0021097 A1* | 1/2018 | Quaid | G06F 19/00 606/130 |

OTHER PUBLICATIONS

Frangi, A.F. et al., "Multiscale vessel enhancement filtering", Medical Image Computing and Computer-Assisted Intervention—MICCAI '98 Lecture Notes in Computer Science, vol. 1496, pp. 130-137 (1998).

Canny, J. "A Computational Approach to Edge Detection", IEEE Transactions on Pattern Analysis and Machine Intelligence, vol. 8, No. 6, pp. 679-698 (1986).

* cited by examiner

RADIATION-FREE REGISTRATION OF AN OPTICAL SHAPE SENSING SYSTEM TO AN IMAGING SYSTEM

CROSS-REFERENCE TO PRIOR APPLICATIONS

This application is the U.S. National Phase application under 35 U.S.C. § 371 of International Application Serial No. PCT/EP2014/076156, filed on Dec. 2, 2014, which claims the benefit of European Patent Application No. 13196480.1, filed on Dec. 10, 2013. These applications are hereby incorporated by reference herein.

FIELD OF THE INVENTION

The invention relates to the field of a registration system, a registration method and a registration computer program for registering a tracking system to an imaging system. The invention relates further to the field of an imaging system and an imaging method for imaging an object. The invention relates also to the field of an interventional system comprising the imaging system and to an interventional device for use in the interventional system.

BACKGROUND OF THE INVENTION

WO 2007/115825 A1 discloses an augmentation device for registering an image of a camera with an intraoperative image for image guided surgery. The augmentation device comprises a camera, an imaging device for intraoperatively generating a three-dimensional or four-dimensional image and a tracking system for tracking the camera and the imaging device. By tracking the imaging device and the camera they can be registered such that an image generated by the camera and an image generated by the imaging device can be simultaneously visualized in a same coordinate system.

WO 2013/102827 A1 discloses a position determining apparatus for determining the position of an interventional instrument within a subject, wherein the interventional instrument comprises a first part to be introduced into the subject and a second part to be outside of the subject, when the first part is introduced into the subject. An image data set providing unit provides an image data set of the interior of the subject, an instrument position providing unit determines a position of the second part of the interventional instrument, and an actual image providing unit provides an actual image of the interventional instrument within the subject. A spatial relation determining unit then determines a spatial relation between the positions of the second part outside the subject and the first part within the subject based on the actual image and the position of the second part, and a position determining unit determines the position of the first part within the provided image data set depending on the position of the second part and the spatial relation between the first part and the second part.

US 2011/0098553 A1 discloses a method for registering images. An image of a part of a body of a patient and of first markers is obtained by an imaging system defining an image coordinate system. An image guidance system is used for obtaining location images showing second markers which are positioned at locations which are known relative to the positions of the first markers. The image guidance system defines a location coordinate system, wherein the image coordinate system and the location coordinate system are automatically registered based on the positions of the first and second markers in the images and the known relative positions of these markers.

US 2010/0056904 A1 discloses an interventional system comprising an interventional instrument like a catheter to be navigated from an insertion site to a treatment site within a patient. During the navigation procedure the interventional instrument, which is equipped with an optical fiber member, is tracked by using optical shape sensing (OSS), wherein the tracked location is shown on a magnetic resonance image of the patient. In order to show the location of the interventional instrument tracked by OSS on the magnetic resonance image of the patient, an OSS tracking system for tracking the interventional instrument and a magnetic resonance imaging (MRI) system for generating the magnetic resonance image need to be registered to each other. Thus, an OSS device (e.g. OSS-integrated guide wire or catheter) must be registered with MRI images. In the above prior art system, the MR image registration is performed by marking within the magnetic resonance image a plurality of known points on the optical fiber member of the interventional instrument, wherein the known points carry markers visible in the magnetic resonance image.

Although conventional registration systems solve many of the shape to image registration problems, there may be different scenarios where a different type of registration may be required. E.g., automatic registration may be desirable in certain cases, further reduction of radiation may be preferable, or the imaging device (e.g. a C-arm device) may be mobile and registration may have to be re-applied whenever the device is moved, or the shape sensing system may be mobile and registration may need to be updated multiple times when the system is moved to another location in the operating room. Furthermore, if X-ray imaging system is being used, the user may prefer to use only one view and does not want to acquire an x-ray image from another angle, or the user may want to see the shape-enabled device registered before the x-ray image is acquired.

SUMMARY OF THE INVENTION

It is an object of the present invention to provide an automatic registration system, a registration method and a registration computer program for registering an imaging device for generating an image of an object with a tracking device for tracking the location of the object, wherein no radiation is necessary for registration.

It is another object of the present invention to provide an automatic registration system, a registration method and a registration computer program for registering an imaging device for generating an image of an object with a tracking device for tracking the location of the object, wherein a single C-arm position or view is sufficient for registration.

It is further object of the present invention to provide an automatic registration system, a registration method and a registration computer program for registering an imaging device for generating an image of an object with a tracking device for tracking the location of the object, wherein movement of the imaging device and/or OSS device can be efficiently handled.

This object is achieved by a registration system according to a representative embodiment, an imaging system according to a representative embodiment, an interventional system according to a representative embodiment, a registration method according to a representative embodiment, an imaging method according to a representative embodiment and a registration computer program according to a representative embodiment.

Accordingly, at least one optical camera is suggested to be used for registration of shape to image. The position of the object (e.g. the OSS device) can be detected based on at least one image of the object generated by the at least one optical camera which may be positioned at a location that is calibrated with the imaging device. By using the optical camera(s), the object can be detected in the camera coordinate system that is pre-registered to the coordinate system of the imaging device. After that, the shape data obtained from the tracking system can be registered with the device or object detected in the optical camera coordinate system that was already calibrated with the coordinate system of the imaging systems.

The proposed solution allows for radiation-free registration of the object with the imaging system (e.g. x-ray system) and an easy update of registration parameters when the tracking system or the imaging system moves. This allows application of the OSS to mobile C-arm systems. Moreover, registration is quickly updated in case the tracking system is mobile and moved during the surgical operation.

Furthermore, a single C-arm position is sufficient to register the tracking system with the imaging system. In x-ray based registration, multiple views may be needed to compute accurate registration parameters in three dimensions (3D). In this case, there is no need to move the C-arm of the imaging system to another position because multiple optical cameras can get 3D information in one setting of the C-arm.

According to a first option, the object detection unit may be adapted to provide the position data of the object based on markers provided on the object. Such markers provide the advantage of an increased accuracy of reconstruction of the object. Moreover, the proposed markers for the object need not be radiopaque. Different light characteristics are sufficient. As such, they can be placed around the device e.g. in plastic, silicone, etc., which will save costs.

According to a second option which can be combined with the above first option, a coordinate system of the at least one optical camera device may be pre-calibrated with a coordinate system of the imaging device, so that the optical shape data generated by the tracking system can be directly translated to the coordinate system of the imaging device.

According to a third option which can be combined with the above first or second option, the at least one optical camera device may be positioned at a location that is calibrated with a C-arm of the imaging device. In a more specific example, the at least one camera may be embedded at a side of a detector rim of the imaging device. Thereby, a predetermined positional relation between the optical camera device(s) and the C-arm can be achieved, which facilitates registration.

According to a fourth option which can be combined with any of the first to third option, the object is adapted to be used in medical intervention and the registration system may be adapted to perform the registration when the object is outside a body of a patient and before insertion of the object into the body of the patient. Thereby, registration can be simplified by merely placing the object into the field of view of the at least one camera device.

According to a fifth option which can be combined with any of the first to fourth option, the registration system may be adapted to propagate obtained registration parameters of the object to other objects. Thereby, inserted objects can be registered without placing them into the field of view of the at least one optical camera device.

According to a sixth option which can be combined with any of the first to fifth option, the object detection unit may be adapted to use a predefined shape of the object for detection and reconstruction to obtain the position of the interventional device that has an optical fiber of the tracking system inside. This allows more accurate detection and reconstruction of the object.

According to a seventh option which can be combined with any of the first to sixth option, the registration unit may be adapted to update or refine registration based on at least one of an image of the imaging device and tracking markers provided on a radiated patient. Thereby, the registration can be continuously updated or refined during operation of the imaging device.

It shall be understood that the registration system of claim 1, the interventional device, the imaging system of claim 9, the interventional system of claim 10, the registration method of claim 11, the imaging method of claim 12 and the registration computer program of claim 13 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Various embodiments of the invention are now described based on an interventional system with an x-ray imaging system having a fixed or mobile C-arm, and an OSS-enabled shape sensing interventional device or instrument (e.g. catheter, guide wire, stent graft etc.).

Figure 1:
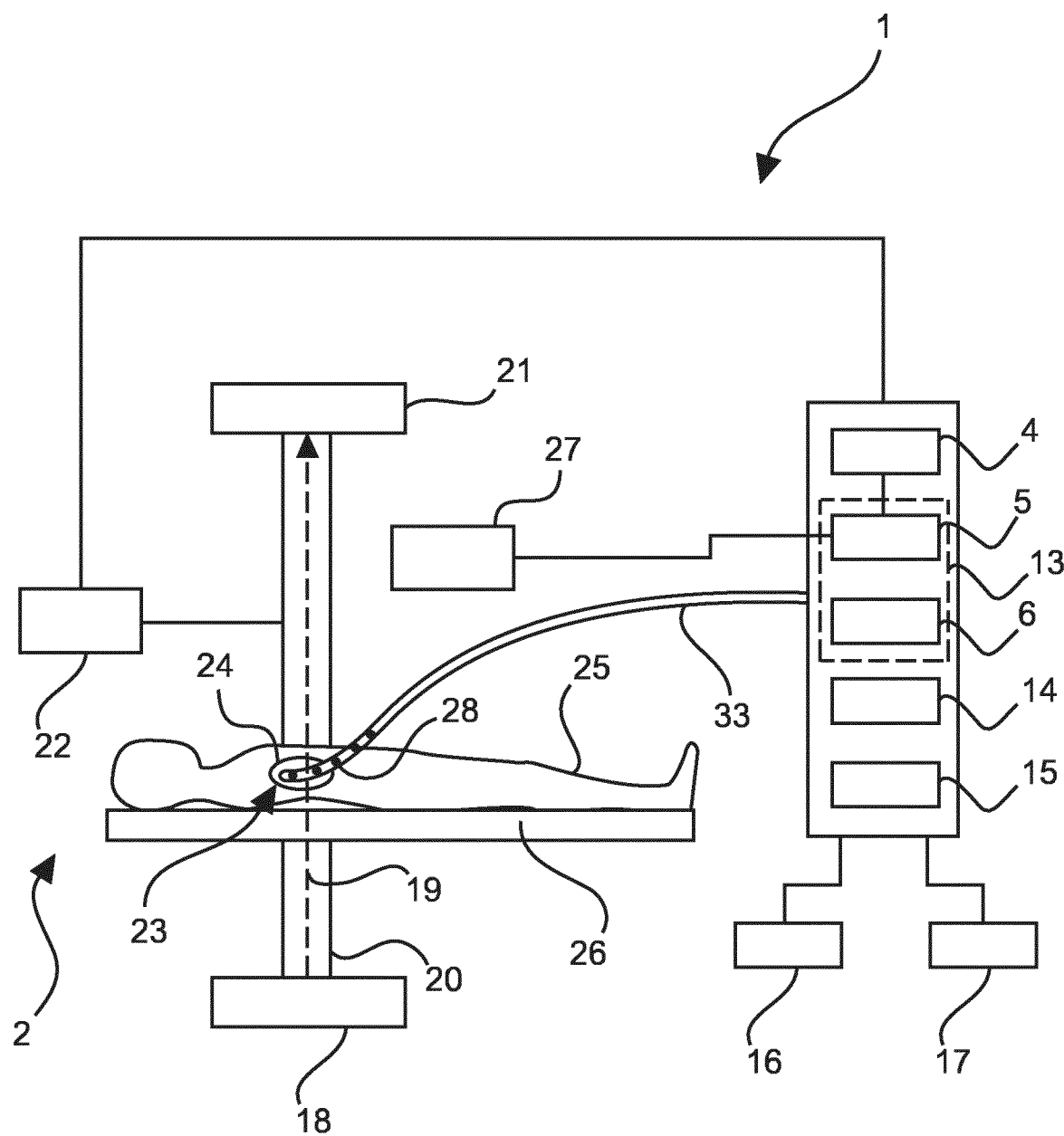
FIG. 1 shows schematically and exemplarily an embodiment of an interventional system according to a first embodiment.

FIG. 1 shows schematically and exemplarily a first embodiment of the interventional system 1 which comprises the interventional instrument for carrying out an interventional procedure. In this embodiment the interventional instrument is a catheter 33, which is controlled by a catheter control unit 15. The catheter control unit 15 and the catheter 33 may be adapted to perform, for instance, an ablation procedure within a heart 24 of a patient 25 lying on a support means like a patient table 26. However, the catheter 33 and the catheter control unit 15 can also be adapted to perform another interventional procedure. Moreover, the interventional system 1 can also comprise another interventional instrument like a needle. In this embodiment, the catheter 33 is adapted to apply a radio frequency (RF) ablation procedure, wherein the catheter control unit 15 is adapted to provide RF energy to ablation electrodes arranged at the tip 23 of the catheter 33. More specifically, the tip 23 of the catheter 33 is positioned against the inner surface of a heart muscle as close as possible to the site of origin of an abnormal rhythm and the catheter control unit 15 is adapted to pass RF current into the area through the tip 23 of the catheter 33 in order to cauterize (burn) and silence the cells responsible for the abnormal heart beat.

For inserting the catheter 33 into the heart 24 a guide wire is used, which is a further interventional instrument and which is equipped with an OSS fiber connected to a tracking device 4 for determining the location of the guide wire within the patient 25, i.e. for determining the position and shape of the guide wire within the patient 25, by OSS. For determining the location of the guide wire within the patient 25 known OSS techniques can be used like the technique disclosed in U.S. Pat. No. 7,772,541 B2 which is herewith incorporated by reference. The guide wire equipped with the OSS fiber and the tracking device 4, in particular, the OSS fiber and the tracking device 4, can be regarded as being a tracking device or OSS system for tracking the location of the guide wire within the patient 25.

The interventional system 1 further comprises an imaging device 2 being, in this embodiment, an x-ray C-arm system. The imaging device 2 comprises an x-ray source 18 generating x-rays 19 traversing the patient 25 and an x-ray detector 21 for detecting the x-rays after having traversed the patient 25. The x-ray source 18 and the x-ray detector 21 are attached to a C-arm 20, which is rotatable around the patient 25 for acquiring x-ray projection images in different projection directions.

Furthermore, one or more optical cameras 27 are used to register a shape coordinate system of the interventional instrument with that of the x-ray imaging system. The optical cameras are pre-calibrated with the x-ray imaging system, so that the detected information in the camera system can directly be translated to the x-ray imaging system. Hence, the at least one optical camera 27 is calibrated with the C-arm 20. The at least one camera 27 is positioned at a respective side of a detector rim and can be used to register the interventional instrument (e.g. the guide wire) before it is being used in the body or to update the registration (i.e. re-registration) when positions of one or both of the imaging system or OSS system are changed. Thus, the OSS system may be mobile or fixed.

The tracking device 4 of the OSS system in FIG. 1 provides optical shape data while the camera system with the at least one optical camera 27 is adapted to provide at least one image of the OSS device (e.g. guide wire) in its field of view. Based on this at least one image, an object detection unit 5 detects the position of the OSS device in the two-dimensional projection images and possibly combines detection results in multiple views to generate a 3D device position in a camera coordinate system or, in another reference system. The two data sets (i.e. optical shape data of the tracking device 4 and the 3D device position derived from images of the at least one camera 27) are supplied as inputs to a registration unit 6.

Thus, the at least one optical camera 27 provides at least one image where the OSS device is visible. The object detection unit 5 may use an object detection algorithm which analyzes the at least one image to find the coordinates of the OSS device in the at least one image. If multiple cameras 27 are used, an object detection process may be provided for each camera image. In the case of multiple cameras, the optical cameras 27 have been calibrated with each other beforehand. From the detection results in each camera view, the object detection unit 5 may compute a 3D position of that part of the OSS device that is visible in the optical cameras 27. This 3D position data can be used for registration with the shape data obtained from the tracking device 4. Further-more, because the geometric transformation between each optical camera 27 and the imaging device 2 is known, the obtained coordinates can be transformed or the final transformation value from registration can be related to the imaging device 2.

In an alternative embodiment, it may be possible to have optical shape data for both OSS devices (i.e. the catheter 33 and the guide wire).

The OSS-enabled interventional instrument (e.g. the guide wire) may have markers 28 that can be detected with the at least one optical camera 27. Based on these markers 28 and multiple camera views, the 3D position of the interventional instrument (e.g. the guide wire) can be reconstructed.

It is to be noted that in FIG. 1, the markers 28 are shown on the catheter 33. In this case, the catheter 33 would be the OSS-enabled interventional instrument with an OSS fiber inside. However, in the described embodiments, the OSS-enabled interventional instrument corresponds to the guide wire which is not shown in FIG. 1. As already mentioned above, even both interventional instruments (i.e. the catheter 33 and the guide wire) may be OSS-enabled instruments.

The imaging device 2 is controlled by an imaging device control unit 22, which receives detection values from the x-ray detector 21 and generates two-dimensional projection images based on the received detection values. The two-dimensional projection images are provided to an object detection unit 5 for detecting the guide wire in the two-dimensional projection images, so that the initial registration based on the image of the at least one optical camera 27 can be refined.

Furthermore, the interventional system 1 comprises a user interface which allows a user to interact with the system by using an input unit 16 like a keyboard, a computer mouse, a touch screen, et cetera and a display 17.

Because the at least one optical camera 27 needs line-of-sight view, the device to be registered (i.e. the guide wire) must be visible by the camera(s) 27. This means that when the device to be registered is inside the body, registration can only be done via other OSS devices that are outside the body of the patient 25. Therefore, keeping one OSS device outside the body can be considered. In the following description, it is assumed that once an OSS device is registered with the x-ray imaging system, that registration can be propagated to other OSS devices, whether they are in the body or outside, by using the knowledge of spatial relations between the OSS devices, especially by using the knowledge of relative location of fixtures in the OSS system. Thus, the OSS system may comprise several OSS devices, wherein the spatial relation between the OSS devices is known. At least one OSS device may be outside the body and used for registering the OSS device with the imaging device by using the optical camera device. Since the spatial relations between the OSS devices is known, the registration between the outside OSS device and the imaging system can be propagated to one or several other OSS devices inside the body. The spatial relations between the OSS devices may be known from calibration measurements. In particular, the OSS system may comprise an attaching element with several slots, which may be regarded as being fixtures, to which the OSS devices may be attached. The locations of the slots relative to each other may be known from a calibration measurement. Moreover, since the fiber axes of the OSS devices may not be aligned in the same way at the positions of the slots, also the rotational positions of the OSS devices, especially of the fiber axes, may be determined by calibration measurements. This information can define the spatial relation between the OSS devices and can be used for propagating a registration with the imaging device from one OSS device to another OSS device.

The interventional system 1 further comprises a registration unit 6 for determining registration parameters defining a registration of the OSS device with the imaging device 2, wherein the registration unit 6 is adapted to determine the registration parameters by calculating a spatial transformation between a shape coordinate system defined by the tracking system (i.e. OSS system) and a coordinate system of the imaging device 2.

After the registration has been completed, the guide wire can be moved within the patient 25, wherein during the movement the tracking device 4 can track the location of the guide wire within the patient 25 and the tracked location of the guide wire can be shown on the two-dimensional projection images without necessarily acquiring these projection images again. It is therefore not necessary to continuously acquire two-dimensional projection images for determining the location of the guide wire within the patient 25 relative to the internal anatomy of the patient 25.

The object detection unit 5 and the registration unit 6 can be regarded as forming a registration system 13 for registering the imaging device 2 with the 3D optical shape sensing data of the OSS device, as obtained from the tracking system.

Figure 2:
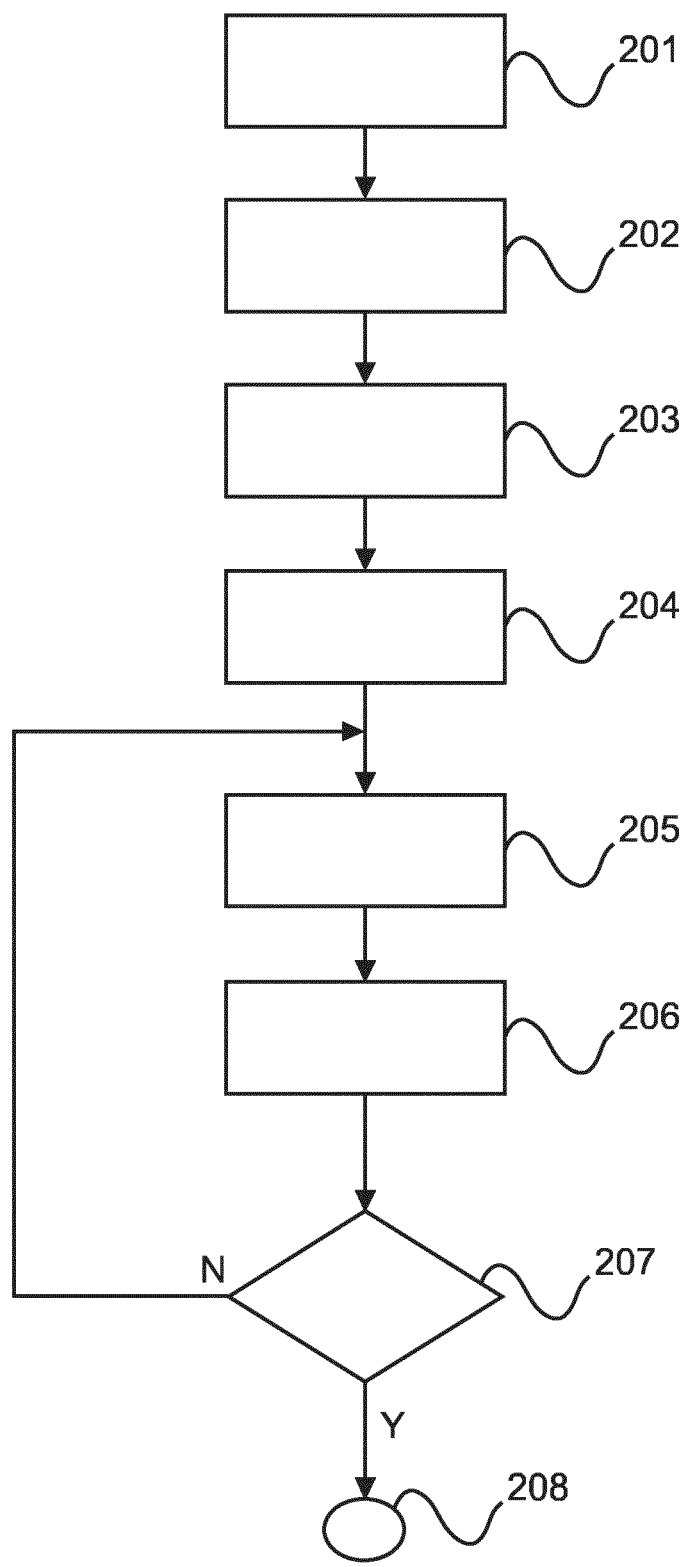
FIG. 2 shows a flowchart exemplarily illustrating a second embodiment of an imaging method for imaging a guide wire.

In the following an imaging method for monitoring an interventional procedure according to a second embodiment will exemplarily be described with reference to a flowchart shown in FIG. 2.

In step 201 the OSS device (i.e. the guide wire in the embodiments) is arranged in the field of view of the at least one optical camera 27 and the optical camera(s) 27 generate at least one image of the OSS device. In step 202 the object detection unit 5 detects the OSS device in the image(s), generate(s) (3D) position data for a (3D) reconstruction of the guide wire, and provides a representation of the guide wire based on the image(s) generated by the optical camera(s) 27 and the shape data obtained from the tracking device 4. In step 203 the registration unit 6 determines registration parameters defining a registration of the imaging device 2 with the 3D optical shape sensing data of the OSS device. Steps 201 to 203 can be regarded as forming a registration method, which may be performed during a calibration procedure, in which the interventional system is calibrated, before the guide wire is inserted into the patient 25.

After the registration parameters have been determined, the patient 25 can be arranged on the support means 26 within the field of view of the imaging device 2 such that the imaging device 2 can generate a two-dimensional projection image of a region of interest within the patient 25 in step 204. The region of interest is preferentially the region within the patient 25, through which the guide wire should be moved. Then, the guide wire can be introduced into the patient 25 and during the introduction of the guide wire and the movement of the guide wire within the patient 25 the location of the guide wire is tracked by the tracking device 4 in step 205. In step 206 the location of the guide wire within the two-dimensional projection image, which has been acquired in step 204, is determined based on the tracked location of the guide wire and the determined registration parameters by a location determination unit 14 and the display 17 shows the determined location of the guide wire within the two-dimensional projection image. In step 207 it is checked whether the imaging of the location of the guide wire within the two-dimensional projection image should be stopped. For instance, it is checked whether the user has input into the interventional system via the input unit 16 that the imaging of the location of the guide wire within the two-dimensional projection image should be stopped. If this is the case, the method ends in step 208. Otherwise, the method continues with step 205. In particular, steps 205 and 206 are continuously performed in a loop, until the imaging of the location of the guide wire within the two-dimensional projection image should stop. By performing steps 205 and 206 in a loop during the movement of the guide wire within the patient 25, the user can monitor the movement of the guide wire within the patient 25 in real time, without necessarily acquiring real time x-ray images. In a further embodiment it can further be checked in step 207 whether the field of view of the imaging device has been modified, wherein in this case the method may continue with step 204.

In case a re-registration should be necessary, e.g. because of a motion of the imaging system and/or motion of the OSS system, then the procedure may loop back step 201 in order to also repeat the registration process. This could be achieved by adding another decision step (e.g. "re-registration required?") in the backward branch from step 207 to step 205. If no re-registration is required, the procedure continues at step 205. Otherwise, if a re-registration is required, the procedure continues at step 201.

There are various ways to complete the optical camera based registration of the OSS device (e.g. the guide wire). As a first option, a user (e.g. a member of the medical staff) may hold the OSS device under the optical camera(s) 27 and the OSS device is detected by the object detection unit 5. The detection results may be displayed on the display 17 of the user interface of FIG. 1, and when detection is satisfactory, registration is performed by computing a transformation between the coordinate systems of the tracking system and the imaging system is computed.

When a mobile OSS system or a mobile C-arm is moved, a similar procedure can be performed. An OSS-enabled device that is outside the body is picked up by the at least one optical camera 27 and registered to the imaging system.

As another option, instead of holding the OSS device under the at least one optical camera 27, the OSS device can be laid down on the patient table 26 or on the patient 25, and registration can be done from there.

If the OSS device has the markers 28 visible in optical cameras for more accurate 3D reconstruction, these markers 28 can be placed around the device during device manufacturing and can be made e.g. from plastic or silicone. They don't have to have any radiopacity. This is an advantage as it does not modify any handling characteristics and it does not add additional cost. The markers can be just colored bars with pre-defined distance that can be used by an algorithm to allow detection in camera images picked up by the optical camera(s) 27.

As a further option, the OSS device may be placed in a predefined shape and the object detection unit 5 uses this predefined shape to be able to detect the OSS device and reconstruct it in 3D more accurately.

When a mobile C-arm is used with a fixed OSS-system, optical shape and X-ray systems can be registered at any place in the operating room and the mobile C-arm position can be automatically localized. This location information can be used to update other parameters, such as x-ray/CT (computed tomography) registration that might have been done at the start of the intervention when the mobile C-arm system was in another location in the room. This option opens up the possibility of using OSS in a mobile C-arm environment.

There can even be multiple OSS devices in the view of the optical camera(s) 27. In such cases, marker correspondences in different views can be used to differentiate the objects or if each OSS device has different types of markers, then this information can be used to separate the OSS devices.

The proposed registration system provides a fully automatic solution for the three-dimensional OSS to two-dimensional x-ray image registration.

If the markers 28 are used, a marker-based reconstruction can be determined by a curve fitting procedure, wherein higher-order approximations of the device can be used. The curve can be fitted to the added markers such that the resulting curve achieves the highest intensity difference from the image elements, which are preferentially pixels, adjacent to the image elements on the curve. Also other measures can be used for fitting the curve, wherein the curve is determined such that the respective measure is optimized, i.e. minimized or maximized. For instance, the difference between the sum of a vesselness response for all image elements on the respective curve and the sum of the vesselness response of all neighboring image elements can be used as a measure for fitting the curve. Further alternative measures are, for instance, the first derivative, edge responses, et cetera. The vesselness response may be defined as a function of the Hessian matrix as disclosed, for instance, in the article "Model-Based Detection of Tubular Structures in 3D images" by K. Krissian et al., Computer Vision and Image Understanding, volume 80, number 2, pages 130 to 171 (2000) or in the article "Multiscale vessel enhancement filtering" by A. F. Frangi et al., Medical Image Computing and Computer-Assisted Intervention—MICCAI'98, Lecture Notes in Computer Science, volume 1496, pages 130-137 (1998), which are herewith incorporated by reference. The edge response may be determined as disclosed in the article "A Computational Approach To Edge Detection" by J. Canny, IEEE Transactions on Pattern Analysis and Machine Intelligence, volume 8, number 6, pages 679 to 698 (1986), which is also herewith incorporated by reference.

Thus, the camera-visible part of the device in 3D is reconstructed from multiple camera images and directly registered with 3D OSS data. Only a part of the device needs to be visible by the at least one optical camera 27. In this way a registration can be achieved substantially independent of device characteristics, i.e. substantially independently of characteristics of the OSS-tracked device. Moreover, this registration procedure is not limited to a certain imaging modality. Thus, although in the above described embodiments the imaging device is an x-ray C-arm device, in other embodiments also other imaging devices can be registered like other radiographic imaging devices, ultrasound imaging devices, magnetic resonance imaging devices, et cetera.

Thus, the representation may not only be determined based on the markers 28 added to the respective image, but additionally also based on image values of image elements of the respective image obtained from the at least one optical camera 27.

As a further option, the registration unit 6 of FIG. 1 may be adapted to update or refine registration based on the image of the imaging device 2 if that becomes available after insertion of the guide wire or the catheter 33.

As an additional or alternative option, if the patient 25 has markers that are trackable, once the shape and imaging coordinate system is registered, the initial registration can be refined or updated, when the imaging device 2 is moved, by tracking the markers on the patient 25. In particular, the markers on the patient 25 may be tracked by using the optical camera device such that, if the registration process has been completed for a certain position of the imaging device relative to the patient, the spatial relations imaging device—OSS device, imaging device—markers and markers—OSS device may be known. If the imaging device is moved relative to the patient, the spatial relation imaging device—OSS device can be determined, i.e. the registration can be refined or updated, by determining the current spatial relation imaging device—markers based on the current positions of the markers on the patient tracked by the optical camera device and the known spatial relation between the imaging device and the optical camera device and by using this current spatial relation imaging device—markers together with the still known spatial relation markers—OSS device.

Although in above described embodiments the tracking device is adapted to track the device by using OSS, in other embodiments also other tracking techniques can be used like an electromagnetic tracking technique. Moreover, although in above described embodiments the registration is used in an interventional application, in another embodiment the registration can also be used in another application requiring a registration between a tracking device for tracking an object and an imaging device for imaging the object.

After the tracking device (i.e. OSS device) has been registered with the imaging device, the tracked location of the object can also be shown in further images, which have not been acquired by the imaging device, but by a further imaging device, if the imaging device, which has been registered to the tracking device, and the further imaging device are registered to each other. These further images can be, for instance, CT images, magnetic resonance images, et cetera, which may have been acquired before an interventional procedure or during an interventional procedure.

Although the interventional system described above with reference to FIG. 1 is adapted to perform an ablation procedure, in other embodiments the interventional system can be adapted to perform another interventional procedure. Moreover, the registration system and the registration method can also be used in other, non-interventional procedures which require a registration of an imaging device with a tracking device.

To summarize, a registration system has been described, for registering an optical shape to an imaging system with an imaging device like an x-ray C-arm device with a tracking device like an optical shape sensing tracking device. One or more optical cameras are used to register the shape coordinate system with that of x-ray. The optical cameras are pre-calibrated with the x-ray system, so that detected position information in the camera system can directly be translated to the x-ray system.

It is to be noted that the present invention is not restricted to registration of shape to x-ray images. Other types of medical images may be MR images, CT images, ultrasound images, etc.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a representation of the object in the image based on the added markers, et cetera performed by one or several units or devices can be performed by any other number of units or devices. The control of the registration system in accordance with the registration method and/or the control of the imaging system in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A registration system for registering an imaging device for generating an image of an object that includes an optical shape sensing (OSS) device with a tracking device that uses optical shape sensing to obtain shape data for tracking a location of the object within a field of view of the imaging device, the registration system comprising:
   at least one optical camera device having a camera coordinate system, different from a coordinate system of the imaging device, the at least imaging device for generating at least one optical camera image of the object, wherein the camera coordinate system is pre-registered to the coordinate system of the imaging device;
   an object detection unit executed by a hardware processor to detect, within the at least one optical camera image, the object that includes the OSS device in the at least one optical camera image, wherein the object detection unit is adapted to analyze the at least one optical camera image of the object to obtain position data of the object within the at least one optical camera image; and
   a registration unit executed by a hardware processor to determine registration parameters defining a registration of the tracking device that uses OSS to obtain shape data with the imaging device, different from the at least one optical camera device, wherein the registration unit is adapted to determine the registration parameters based on the position data of the object obtained via the object detection unit and based on a geometric transformation between the at least one optical camera device, different from the imaging device, and the imaging device.

2. The registration system as defined in claim 1, wherein the object detection unit is adapted to provide the position data of the object based on markers provided on the object.

3. The registration system according to claim 1, wherein the object is adapted to be used in medical intervention and the registration system is adapted to perform the registration when the object is outside a body of a patient and before insertion of the object into the body of the patient.

4. The registration system according to claim 1, wherein the registration system is adapted to propagate obtained registration parameters of the object to another object by using a known spatial relation between these objects.

5. The registration system according to claim 1, wherein the object detection unit is adapted to use a predefined shape of the object for obtaining the position data.

6. The registration system according to claim 1, wherein the registration unit is adapted to update or refine registration based on at least one of an image of the imaging device and tracking markers provided on a radiated patient.

7. An imaging system for imaging an object, the imaging system comprising:
   an imaging device for generating an image of a region of interest,
   a tracking device for tracking the location of the object in the region of interest,
   a registration system as defined in claim 1 for determining registration parameters,
   a location determination unit executed by the hardware processor to determine the location of the object within the image of the region of interest based on the tracked location of the object and the determined registration parameters.

8. An interventional system comprising:
   an interventional instrument for carrying out an interventional procedure; and
   an imaging system for imaging the interventional instrument as defined in claim 7.

9. The interventional system according to claim 8, wherein the interventional instrument comprises a plurality of registration markers with a light characteristic different from that of the interventional instrument so that said registration markers are detectable based on an image taken by an optical camera device during registration of an imaging device for generating an image of the interventional instrument with a tracking device for tracking the location of the interventional instrument within a field of view of the imaging device.

10. The interventional system according to claim 9, wherein the registration markers are made of a plastic material or silicone.

11. A method for registering an imaging device for generating an image of an object that comprises an optical shape sensing (OSS) device with a tracking device that uses optical shape sensing to obtain shape data for tracking a location of the object in a field of view of the imaging device, the method comprising:
   generating at least one optical camera image of the object by using at least one optical camera device having a camera coordinate system, different from a coordinate system of the imaging device, wherein the camera coordinate system is pre-registered to the coordinate system of the imaging device;
   analyzing, via an object detection unit, the at least one optical camera image to detect within the at least one optical camera image, the object that includes the OSS device in the at least one optical camera image, and to obtain position data of the object within the at least one optical camera image; and
   determining, via a registration unit, registration parameters defining a registration of the tracking device that uses OSS to obtain shape data with the imaging device, different from the at least one optical camera device, based on the position data of the object obtained via the object detection unit and based on a geometric transformation between the at least one optical camera device, different from the imaging device, and the imaging device.

12. An imaging method for imaging an object, the imaging method comprising:
   generating an image of a region of interest by an imaging device;

tracking the location of the object in the region of interest by a tracking device, determining registration parameters by the method as defined in claim 11; and generating a location image indicating the location of the object within the image of the region of interest based on the tracked location of the object, the image of the region of interest and the determined registration parameters.

13. A registration system for registering an imaging device for generating an image of an object that includes an optical shape sensing (OSS) device with a tracking device that uses optical shape sensing to obtain shape data for tracking a location of the object within a field of view of the imaging device, comprising:

a tangible and non-transitory memory that stores instructions, which when executed by a processor cause the processor to:

generate at least one optical camera image of the object by using at least one optical camera device having a camera coordinate system, different from a coordinate system of the imaging device, wherein the camera coordinate system is pre-registered to the coordinate system of the imaging device;

analyze, via an object detection unit, the at least one optical camera image to detect within the at least one optical camera image, the object that includes the OSS device in the at least one optical camera image, and to obtain position data of the object within the at least one optical camera image; and determine, via a registration unit, registration parameters defining a registration of the tracking device that uses optical to obtain shape data with the imaging device, different from the at least one optical camera device, based on the position data of the object obtained via the object detection unit and based on a geometric transformation between the at least one optical camera device, different from the imaging device, and the imaging device.

14. The registration system as defined in claim 13, wherein the object detection unit is adapted to provide the position data of the object based on markers provided on the object.

15. The registration system according to claim 13, wherein the object is adapted to be used in medical intervention and the registration system is adapted to perform the registration when the object is outside a body of a patient and before insertion of the object into the body of the patient.

16. The registration system according to claim 13, wherein the registration system is adapted to propagate obtained registration parameters of the object to another object by using a known spatial relation between these objects.

17. The registration system according to claim 13, wherein the object detection unit is adapted to use a predefined shape of the object for obtaining the position data.

18. The registration system according to claim 13, wherein the registration unit is adapted to update or refine registration based on at least one of an image of the imaging device and tracking markers provided on a radiated patient.

* * * * *